United States Patent [19]

Levy

[11] 4,349,538

[45] * Sep. 14, 1982

[54] NUCLEASE-RESISTANT HYDROPHILIC COMPLEX OF POLYRIBOINOSINIC-POLYRIBOCYTIDYLIC ACID

[75] Inventor: Hilton B. Levy, Bethesda, Md.

[73] Assignee: The United States of America as represented by the Secretary of the Department of Health and Human Services, Washington, D.C.

[ * ] Notice: The portion of the term of this patent subsequent to Apr. 20, 1993, has been disclaimed.

[21] Appl. No.: 208,029

[22] Filed: Nov. 18, 1980

Related U.S. Application Data

[63] Continuation-in-part of Ser. No. 101,074, Dec. 7, 1979, abandoned.

[51] Int. Cl.$^{3}$ ..................... A61K 45/02; A61K 37/02; C07C 103/52

[52] U.S. Cl. ............................... 424/85; 260/112.5 R; 424/177; 424/180; 536/27; 536/28; 536/29

[58] Field of Search ................ 424/85, 177, 180, 274; 260/112.5 R; 536/27–29

[56] References Cited

U.S. PATENT DOCUMENTS 4,024,241 5/1977 Levy .................................... 536/28

OTHER PUBLICATIONS

Chemical Abstracts, vol. 92, Abstract No. 174365n, p. 37, 1980.

Chemical Abstracts, vol. 92, Abstract No. 104368s, p. 57, 1980.

Chemical Abstracts, vol. 93, Abstract No. 197823v, p. 61, 1980.

Chemical Abstracts, vol. 91, Abstract No. 321y, p. 319 1979.

Chemical Abstracts, vol. 92, Abstract No. 600v, p. 596, 1980.

Derwent Abstracts, Belgium Pat. No. 833838, 1976.

*Primary Examiner*—Blondel Hazel

*Attorney, Agent, or Firm*—Holman & Stern

[57] ABSTRACT

A nuclease-resistant hydrophilic complex of polyriboinosinic-polyribocytidylic acid, poly-1-lysine, and carboxymethylcellulose, and injectable preparations thereof in a pharmaceutically acceptable aqueous carrier such as saline solution. When administered to a human or non-human primate host, the complex is effective in inducing the synthesis in such host of antiviral levels of interferon.

19 Claims, No Drawings

NUCLEASE-RESISTANT HYDROPHILIC COMPLEX OF POLYRIBOINOSINIC-POLYRIBOCYTIDYLIC ACID

CROSS-REFERENCE TO RELATED APPLICATION

This is a continuation-in-part of application Ser. No. 101,074 filed Dec. 7, 1979, now abandoned.

BACKGROUND OF THE INVENTION

1. Field of the Invention

This invention relates to an interferon-inducing complex, and more particularly, to a nuclease-resistant hydrophilic complex of polyriboinosinic-polyribocytidylic acid useful for inducing the synthesis of interferon in primates, including non-human primates.

2. Description of the Prior Art

The synthetic double-stranded RNA, polyriboinosinic-polyribocytidylic acid (hereinafter "In.Cn") is a material known for its activity as an interferon inducer, antiviral, and antitumor agent in rodents. This material, the method for its preparation, and its aforementioned activity in rodents, are described, for example, by Field, et al., Proceedings of the National Academy of Sciences, Volume 58, Pages 1004–1010 (1967), and Levy, et al., Proceedings of the National Academy of Sciences, Volume 62, No. 2, pages 357–361 (1969). In man, however, In.Cn has proven to be a poor interferon inducer and has no detectable antitumor action. There is present in human serum a high level of hydrolytic activity against In.Cn which conceivably could be responsible for the low activity of the drug in man. Although several attempts have been made to prepare stabilized In.Cn derivatives, none of these compounds has proved to be fruitful. Moreover, previous attempts have been made to induce interferon in non-human primates with In.Cn, but little or no interferon was produced. While in man and non-human primates topical application has had some very minor success in prophylaxis of some viral diseases, there has been no success in altering the course of systemic clinical disease with interferon inducers.

In connection with its activity in rodents, In.Cn of relatively low molecular weight, i.e., within the range from about $1\times10^5$ to about $3\times10^5$ daltons, has previously been found to have its activity enhanced by complexing it with high molecular weight poly-d-lysine, i.e., having a molecular weight of approximately 180,000 daltons. It was not possible, however, to use the same procedure with a high molecular weight In.Cn, i.e., having a molecular weight within the range of from about $7\times10^5$ to about $1\times10^7$ daltons. Further, since the amino acid, d-lysine, is not a natural occurring amino acid, it was felt that high molecular weight poly-d-lysine would very likely be restrictively antigenic.

In U.S. Pat. Nos. 3,952,097 and 4,024,241, and various corresponding foreign patents claiming priority therefrom, of all of which I am also the sole inventor, there are described and claimed similar complexes to that of the present invention, and the use of said compounds. However, in all of these patents, the poly-1-lysine component of the complex is disclosed as having a molecular weight range of from about 2,000 daltons to about 5,000 daltons. After further research and development, it has now unexpectedly been found that the complexes disclosed and claimed in these patents are inoperative. Apparently, the supplier of the poly-1-lysine used in the original research mislabeled the molecular weight range of the supplied compound. This was discovered after attempts to replicate the original experimentation with poly-1-lysine having a true molecular weight of about 2,000 to about 5,000 daltons were unsuccessful.

SUMMARY OF THE INVENTION

This invention provides a nuclease-resistant hydrophilic complex of high molecular weight In.Cn with relatively low molecular weight poly-1-lysine and carboxymethylcellulose. The In.Cn of the complex has a molecular weight in the range of from about $7\times10^5$ daltons to about $1\times10^7$ daltons, and the poly-1-lysine of such complex has a molecular weight within the range from about 13,000 daltons to about 35,000 daltons with a range of about 17,000 daltons to about 28,000 daltons being preferred and a range of about 27,000 daltons to about 28,000 daltons being optimum. At molecular weights below about 13,000 daltons interferon is not produced. At molecular weights above about 35,000 daltons the complex produced is restrictively antigenic. In another embodiment, a poly-1-lysine range of 13,000 to 28,000 daltons may be used.

DESCRIPTION OF THE PREFERRED EMBODIMENTS

Non-toxic and non-antigenic injectable preparations of the complex of the present invention are preferably prepared by providing separate solutions of each of the three components of the complex in a pharmaceutically acceptable aqueous carrier such as pyrogen-free saline, and first mixing the poly-1-lysine solution with the carboxymethylcellulose solution, preferably by slowly pouring the former into the latter with stirring, and continuing the stirring to redissolve any precipitate thereby formed. For best results, such stirring is preferably continued for a period of time sufficient to achieve minimum turbidity in the solution, which generally requires 2 to 3 days. To the resulting solution of poly-1-lysine-carboxymethylcellulose complex, is then added the In.Cn solution, preferably followed by an additional 2 to 3 days of stirring, to form the final solution of In.Cn-poly-1-lysine-carboxymethylcellulose complex, abbreviated as poly(ICLC). The carboxymethylcellulose, which is a hydrophilic material negatively charged at a neutral pH is an essential part of the complex, since without its presence, the In.Cn and the poly-1-lysine would form an intractable precipitate. Moreover, the above-described order of addition of the components of the complex, i.e., first forming the poly-1-lysine-carboxymethylcellulose complex and thereafter adding the In.Cn thereto to form the final poly(ICLC) complex, is critical to the preparation of the complex since any other order of addition would result in the formation of an intractable precipitate.

While the In.Cn, poly-1-lysine and carboxymethylcellulose may each be used in a wide range of ratios in preparing nuclease-resistant hydrophilic In.Cn complexes, the injectable complex preparations in accordance with the present invention preferably contain 1–4 mg/ml of the In.Cn, 0.75–3 mg/ml of the poly-1-lysine and 0.25–1 percent by weight of the carboxymethylcellulose. A particularly suitable injectable preparation has been found to be a saline solution containing 2 mg/ml of In.Cn, 1.5 mg/ml of poly-1-lysine and 0.5 percent by weight of carboxymethylcellulose.

The In.Cn complexes of the present invention have been found to be four to ten times more resistant to hydrolysis by pancreatic ribonuclease and human serum than the parent uncomplexed In.Cn. When administered by injection to non-human primates such as monkeys or chimpanzees in dosages sufficient to provide from about 1 to about 5 mg of In.Cn per kg of body weight, and to humans in dosages sufficient to provide from about 0.3 to about 2 mg of In.Cn per kg of body weight, with a preferred dose less than 1 mg, the complexes of the present invention are non-toxic and non-antigenic and will induce the synthesis of interferon in significant levels associated with antiviral effects. For example, when administered by injection in the above dosages, the In.Cn complexes of the present invention are effective in protecting primates, including humans, against such viral diseases as yellow fever virus, rabies, hepatitis and viral encephalitides; and in protecting non-human primates against Simian hemorrhagic fever virus. The preferred route of injection is either intravenously or intrathecally, with treatment preferably being given at a frequency of from every other day to daily in a dose sufficient to provide about 3 mg of In.Cn per kg of body weight in the case of non-human primates and about 0.5 mg of In.Cn per kg of body weight in the case of humans.

The In.Cn complexes of the present invention are also expected to be effective for treating both humans and non-human primates, when administered by topical application, against viral herpes diseases, such as herpetic keratoconjunctivitis (e.g., 1–2 drops in each eye every 6 hours of the above-described preparation of the complex), herpes virus of the genital organs, and cold sores; and when administered by inhalation, against various viral respiratory diseases, such as the common cold and influenza.

In the following examples, the In.Cn was prepared from an approximately equimolar mixture of polyriboinosinic acid and polyribocytidylic acid. Both of these materials were heterogeneous in size, with molecular weights in excess of $10^5$. They were dissolved at a concentration of 4 mg/ml in 0.85 percent NaCl. The solutions were warmed to 30° C. and the polyribocytidylic acid was poured into the polyriboinosinic acid while constantly being mixed. There was a hypochromic shift of about 35 percent, indicating that the base-paired double-stranded structure had formed.

EXAMPLE I—PREPARATION

The following solutions in pyrogen-free saline, 0.85 percent NaCl were prepared: (1) 500 ml of In.Cn at 4 mg/ml; (2) 250 ml of 2 percent carboxymethylcellulose (7 HSP, high viscosity); and (3) 250 ml of poly-1-lysine (molecular weight about 27,000 daltons) at 6 mg/ml. The poly-1-lysine solution was poured slowly into the carboxymethylcellulose solution with stirring. A precipitate was formed which dissolved after two additional days of stirring. The In.Cn solution was then poured into the solution of the poly-1-lysine-carboxymethylcellulose complex and stirred for an additional two days, to form a preparation of In.Cn-poly-1-lysine-carboxymethylcellulose complex. Such preparation contained 2 mg/ml of In.Cn, 1.5 mg/ml of poly-1-lysine, and 0.5 percent by weight of carboxymethylecellulose. As assayed by the rate of increase in optical density at 260 mμ, the In.Cn complex so prepared was 4 to 10 times more resistant to hydrolysis by pancreatic ribonuclease and human serum than was the parent uncomplexed In.Cn.

EXAMPLE II—PREPARATION

For 1 liter of poly(ICLC) four solutions were prepared as follows in sterile pyrogen free 0.15 M NaCl.

(a) Poly I (Ca 9s)—1.0 g/250 ml. The pH of this material may need to be adjusted to 8.8 to ensure solution. Sterilize by filtration.

(b) Poly C (Ca 9s)—0.93 g/250 ml. Sterilize by filtration (c) Poly-1-lysine. H Br. mol. wt. about 27,000 daltons. 1.5 g/250 ml. Sterilize by filtration.

(d) Carboxymethylcellulose (CMC) 7H3SF. 5.0 g/250 ml saline. Stir till dissolved. Sterilize by autoclaving.

Pour (a) into (b), with stirring. Stir for 2–3 hours. Pour (c) into (d) slowly (30 minutes). A heavy turbidity or slight precipitate will form, which will redissolve in 24–48 hours of stirring, leaving an opalescent solution. Pour the poly(I).poly(C) slowly into the poly-1-lysine-CMC. Stir overnight. Adjust pH to Ca 7.8 with sterile 0.1 N in NaOH.

This material contains $3\times10^{-3}$ M poly I.poly C, $7\times10^{-3}$ M poly-1-lysine and $7\times10^{-3}$ M CMC, expressed as carboxymethyl content. It is stable for at least one year at 4° C., and should not be frozen.

The molar ratio of nucleotide $PO_4$ in poly(ICLC) to $\epsilon$ amino group of lysine is 1:1. T'so, et al. showed that in poly(I).poly(C) poly-1-lysine without CMC the saturating level of poly-1-lysine is at a $PO_4$:$NH_2$ ratio of 2:1. Therefore, there is excess $\epsilon$ amino linkages in poly(ICLC). It is reasonable to suggest that this $\epsilon$ $NH_2$ capacity is bound to the CMC in some way, giving a 4 component complex containing poly I, poly C, poly-1-lysine, and CMC.

EXAMPLE III—EFFECT OF MOLECULAR WEIGHT OF POLY-L-LYSINE

The following studies done with complexes made with a polynucleotide and poly-1-lysine of a mol. wt. from about 2,000 daltons to about 27,000 daltons, shows comparative results for complexes in which the sizes of the poly I and poly C were kept constant at about 9S and the molecular weight of the poly-1-lysine was varied over the range of about 2,000 to about 27,000 daltons. It can be seen from the below Table that the abilities of the different complexes to induce interferon is most clearly correlated with their resistance to hydrolysis by pancreatic RNase, with the complex made with a mol. wt. of about 27,000 daltons poly-1-lysine being most resistant and therefore optimum. The lowest effective molecular weight of poly-1-lysine in a complex was about 17,000 daltons, although a complex with minimal results could be achieved with a poly-1-lysine molecular weight of as low as about 13,000 daltons.

TABLE I

Correlation Between Molecular Weight of Poly-l-lysine, Hydrolysis and Interferon Induction in Monkeys by Poly(ICLC)

| Molecular weight of poly-l-lysine | Hydrolysis of poly(ICLC)* | Peak serum interferon levels ($\log_{10}$ units/ml) |
|---|---|---|
| 27,000 | 7.8 | 3.2 |
| 17,000 | 11.4 | 2.0 |
| 3,400 | 27.2 | 1.4 |

TABLE I-continued

| Correlation Between Molecular Weight of Poly-l-lysine, Hydrolysis and Interferon Induction in Monkeys by Poly(ICLC) | | |
|---|---|---|
| Molecular weight of poly-l-lysine | Hydrolysis of poly(ICLC)* | Peak serum interferon levels ($log_{10}$ units/ml) |
| 2,000 | 61.6 | 1.2 |

*Hydrolysis of poly(I) · poly(C) taken as 100%, 20 μg RNase/ml, 1 hour, 25° C.

EXAMPLE IV—APPLICATION

The preparation prepared in accordance with Example I was injected intravenously into four chimpanzees and 25 Rhesus monkeys in doses sufficient to provide 3 mg/kg of In.Cn. Representative serum interferon levels measured prior to the treatment and eight, twenty-four and forty-eight hours following the treatment are given in Table II below.

TABLE II

| Time | Serum Interferon Level (I.U./ml) | |
|---|---|---|
| | Rhesus Monkey | Chimpanzee |
| Pretreatment | <10 | 10 |
| 8 hours | 125–6000 | 600 |
| 24 hours | 80–250 | 125 |
| 48 hours | 0–125 | 10 |

Comparable levels of interferon were found in cerebro-spinal fluid when the preparation was injected intrathecally in chimpanzees and Rhesus monkeys. No overt toxicity was seen at these levels when the preparation was administered either intravenously or intrathecally.

EXAMPLE V—APPLICATION

The preparation of Example I was injected intravenously into four Rhesus monkeys in a dose sufficient to provide 3 mg/kg of In.Cn eight hours before an LD 100 challenge of Simian hemorrhagic fever virus, and the dose was repeated several times during the next two weeks. Hundreds of untreated Rhesus monkeys given the same challenge of the virus were all dead in seven to eight days. Of the four treated monkeys, three of them developed no disease. The fourth monkey developed the disease two weeks later, but this disappeared upon additional treatment. This experiment demonstrates that the preparation of the present invention is capable of inducing the synthesis of interferon in primates at levels sufficient to control systemic virus disease.

An analogous protocol was followed using yellow fever virus, rabies, hepatitis, and viral encephalitides in place of the Simian hemorrhagic fever virus, with comparable results.

An analogous protocol may be followed in treating humans against yellow fever virus, rabies, hepatitis, and viral encephalitides, but with the dosage of the preparation of Example I reduced to one sufficient to provide approximately 0.3 mg/kg of In.Cn.

EXAMPLE VI—APPLICATION

The preparation of Example I was injected into groups of 4 people at each of several different dose levels, and the interferon produced was measured in their serum, with the following results:

TABLE III

| Dose (mg/m$^2$) | Mean peak units of interferon per ml serum |
|---|---|
| 0.5 | 15 |
| 2.5 | 15 |
| 7.5 | 198 |
| 12 | 1940 |
| 18 | 4473 |
| 27 | 5820 |

EXAMPLE VII—PREPARATION

A complex was prepared according to Example I, but where the concentration of polyriboinosinic acid-polyribocytidylic acid was 6 mg/ml, the concentration of CMC was 1.5%, and in which the CMC was of low viscosity. The resulting complex was an effective interferon inducer in monkeys.

I claim:

1. A nuclease-resistant hydrophilic complex of: relatively high molecular weight polyriboinosinic-polyribocytidylic acid; relatively low molecular weight poly-1-lysine in a range of from about 13,000 daltons to about 35,000 daltons; and carboxymethylcellulose.

2. The complex of claim 1 wherein said polyriboinosinic-polyribocytidylic acid has a molecular weight in the range of from about $7 \times 10^5$ daltons to about $1 \times 10^7$ daltons.

3. The complex of claim 2 wherein the poly-1-lysine has a molecular weight of from about 17,000 daltons to about 28,000 daltons.

4. The complex of claim 3 wherein the poly-1-lysine has a molecular weight of from about 27,000 daltons to about 28,000 daltons.

5. An injectable preparation in a pharmaceutically acceptable carrier of the complex of claim 1 whose unit dosage is sufficient to induce the synthesis of interferon in a mammal into which it is to be injected.

6. An injectable preparation in a pharmaceutically acceptable carrier of the complex of claim 3 whose unit dosage is sufficient to induce the synthesis of interferon in a mammal into which it is to be injected.

7. An injectable preparation in a pharmaceutically acceptable carrier of the complex of claim 4 whose unit dosage is sufficient to induce the synthesis of interferon in a mammal into which it is to be injected.

8. The preparation of claim 6 containing 1 to 4 mg/ml of said polyriboinosinic-polyribocytidylic acid, 0.75 to 3 mg/ml of poly-1-lysine and 0.25 to 1 percent by weight of said carboxymethylcellulose.

9. The preparation of claim 8 containing 2 mg/ml of said polyriboinosinic-polyribocytidylic acid, 1.5 mg/ml of said poly-1-lysine and 0.5 percent by weight of said carboxymethylcellulose.

10. The preparation of claim 8 wherein said carrier is saline solution.

11. A method of inducing the synthesis of interferon in a primate which comprises administering to a primate host a nuclease-resistant hydrophilic complex of relatively high molecular weight polyriboinosinic-polyribocytidylic acid, relatively low molecular weight poly-1-lysine in a range of from about 13,000 daltons to about 35,000 daltons, and carboxymethylcellulose, in a dose sufficient to provide an interferon-inducing amount of said polyriboinosinic-polyribocytidylic acid.

12. The method of claim 11 wherein the poly-1-lysine has a molecular weight of from about 17,000 daltons to about 28,000 daltons.

13. The method of claim 12 wherein the poly-1-lysine has a molecular weight of from about 27,000 daltons to about 28,000 daltons.

14. The method of claim 12 wherein said host is a non-human primate and said complex is administered from every other day to daily in a dose sufficient to provide from about 1 to about 5 mg of said polyriboinosinic-polyribocytidylic acid per kg of body weight.

15. The method of claim 14 wherein said complex is administered from every other day to daily in a dose sufficient to provide about 3 mg of said polyriboinosinic-polyribocytidylic acid per kg of body weight.

16. The method of claim 11, 12 or 13 wherein said host is a human and said complex is administered from every other day to daily in a dose sufficient to provide from about 0.3 to 2 mg of said polyriboinosinic-polyribocytidylic acid per kg of body weight.

17. The method of claim 16 wherein said complex is administered from every other day to daily in a dose sufficient to provide about 1 mg of said polyriboinosinic-polyribocytidylic acid per kg of body weight.

18. The method of claim 11 wherein the poly-1-lysine molecular weight is from about 13,000 to 28,000 daltons.

19. The complex of claim 1 wherein the poly-1-lysine molecular weight is from about 13,000 to 28,000 daltons.

* * * * *